United States Patent [19]

Jones et al.

[11] Patent Number: 4,743,607
[45] Date of Patent: May 10, 1988

[54] CARDIOTONIC TRICYCLIC IMIDAZOLONES

[75] Inventors: Winton D. Jones; George P. Claxton; Richard A. Schnettler; Richard C. Dage, all of Cincinnati, Ohio

[73] Assignee: Merrell Dow Pharmaceuticals Inc., Cincinnati, Ohio

[21] Appl. No.: 55,666

[22] Filed: May 29, 1987

[51] Int. Cl.$^4$ ................. A61K 31/47; C07D 471/04
[52] U.S. Cl. ................................. 514/293; 546/82
[58] Field of Search .................... 546/82; 514/293

[56] References Cited

U.S. PATENT DOCUMENTS

| | | | |
|---|---|---|---|
| 4,532,250 | 7/1985 | Stout | 514/341 |
| 4,668,683 | 5/1987 | Takai et al. | 514/259 |
| 4,668,686 | 5/1987 | Meanwell et al. | 514/293 |
| 4,670,451 | 6/1987 | Vematsu et al. | 514/375 |

OTHER PUBLICATIONS

Hofmann, K., *Imidazole and Its Derivatives*, Part I, Interscience, New York, 1953, pp. 63–64.
Derwent Abstract of USSR 891,671, 12/23/81.

*Primary Examiner*—Richard A. Schwartz
*Attorney, Agent, or Firm*—Stephen L. Nesbitt

[57] ABSTRACT

Tricyclic imidazolones enhance myocardial contractile force and are useful as cardiotonics in the treatment of heart failure. The compounds have the formula:

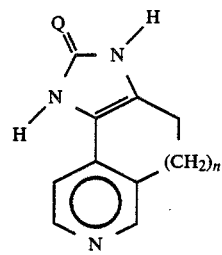

13 Claims, No Drawings

CARDIOTONIC TRICYCLIC IMIDAZOLONES

BACKGROUND OF THE INVENTION

This invention relates to the use of certain tricyclic imidazolones to enhance myocardial contractile force. These compounds are useful as cardiotonics in the treatment of heart failure.

Heart failure is that physiological condition resulting from the inability of the ventricular myocardium to maintain adequate blood flow to the peripheral body tissues and includes congestive heart failure, backward and forward heart failure, right ventricular and left ventricular heart failure, and low-output heart failure. Heart failure can be caused by myocardial ischemia, myocardial infarction, excessive alcohol usage, pulmonary embolism, infection, anemia, arrhythmias, and systemic hypertension. Symptoms include tachycardia, fatigue with exertion, dyspnea, orthopnea, and pulmonary edema.

Treatment involves either removal or correction of the underlying causes or involves control of the heart failure state. Management or control can be accomplished by increasing cardiac output or by decreasing cardiac workload. While workload can be accomplished by reduction of physical activities and physical and emotional rest, increasing cardiac output has traditionally involved digitalis therapy. Digitalis stimulates contractile force of the heart which increases cardiac output and improves ventricular emptying. In this way digitalis therapy normalizes venous pressure and reduces peripheral vasoconstriction, circulatory congestion, and organ hypoperfusion.

Unfortunately, optimal doses of digitalis vary with the patient's age, size, and condition and the therapeutic to toxic ratio is quite narrow. In most patients the lethal dose is only about five to ten times the minimal effective dose with toxic effects becoming apparent at only 1.5 to 2.0 times the effective dose. For these reasons, dose must be carefully tailored to suit the individual and frequent clinical examinations and electrocardiogram is necessary to detect early signs of digitalis intoxication. Despite this care digitalis intoxication is reported in up to one-fifth of hospitalized patients undergoing therapy.

The need for less toxic and more effective cardiotonic agents is readily apparent. Applicants have discovered certain tricyclic imidazolones which possess patent cardiotonic and vasodilation activity and by comparison to digitalis have few toxic effects.

SUMMARY OF THE INVENTION

This invention relates to certain imidazolones of structure 1:

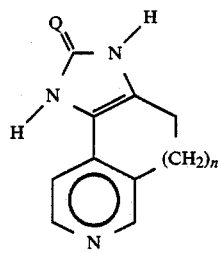

wherein

Q is a divalent sulfur or oxygen atom; and n is 0 or the integer 1 or 2 and the pharmaceutically acceptably salts thereof as well as the use of these compounds as vasodilators, to enhance myocardial contractile force, and to treat heart failure, their pharmaceutical compositions, and the process of their preparation.

DETAILED DESCRIPTION OF THE INVENTION

The imidazole ring of the compounds of structure 1 exist in several tautomeric forms. Throughout this disclosure, the tricyclic imidazolones of structure 1 are intended to include these tautomers as well.

The ring nitrogen atoms of the imidazole ring in the structure 1 compounds can be substituted with a ($C_1$–$C_5$) alkyl group, an alkanoyl group such as an acetyl group, or benzoyl group. These nitrogen substituted compounds are equivalent to the unsubstituted compounds primarily because the substitutent is cleaved upon administration to a patient and also because many of the nitrogen substituted compounds independently possess significant ability to enhance myocardial contractile force and are useful cardiotonic agents.

As is true for most classes of therapeutically effective compounds, certain subclasses and certain species are more effective than others. In this instance those compounds of structure 1 wherein Q is a divalent oxygen atom are preferred. Also preferred are those compounds wherein n is the integer 1. More preferred are those compounds of structure 1 wherein Q is a divalent oxygen atom and n is the integer 1.

The compounds of this invention are useful both in the free base form and in the form of acid addition salts. The acid addition salts are simply a more convenient form for use and, in practice, use of the salt amounts to use of the free base. The expression "pharmaceutically acceptable acid addition salts" is intended to apply to any non-toxic organic or inorganic acid addition salts of the base compounds of formula 1. Illustrative inorganic acids which form suitable salts include hydrochloric, hydrobromic, sulfuric, and phosphoric acids and acid metal salts such as sodium monohydrogen orthophosphate and potassium hydrogen sulfate. Illustrative organic acids which form suitable salts include the sulfonic acids such as methane sulfonic acid and 2-hydroxyethane sulfonic acid. Either the mono- or the di-acid salts can be formed, and such salts can exist in either a hydrated or a substantially anhydrous form. The acid salts are prepared by standard techniques such as by dissolving the free base in aqueous or aqueous-alcohol solution or other suitable solvent containing the appropriate acid and isolating by evaporating the solution, or by reacting the free base in an organic solvent in which case the salt separates directly or can be obtained by concentration of the solution.

The compounds of structure 1 are also acidic and can form pharmaceutically acceptable salts with suitable inorganic bases. These salts include those of the alkali metals such as lithium, sodium, or potassium. These salts can be prepared using conventional means such as by neutralizing a solution of the free acid in a polar solvent with a stoichiometric quantity of base, for example, an alkoxide such as sodium methoxide or potassium ethoxide or a hydride such as lithium hydride. These reactions are preferably carried out in solution. Suitable solvents are, for example, lower alcohols such as methanol, ethanol, isopropanol, or n-propanol; the ketonic solvents such as acetone or methylethylketone; or dimethylformamide (DMF). Typically about 1 molar equivalent of the free acid compound of structure 1 is allowed to react with about 1 molar equivalent of the base for about 1 minute to about 24 hours, preferably about 1 hour, depending on the reactants and the temperature which can be from about −30° C. to about 78° C., preferably about 0° C. to about 25° C. In general the pharmaceutically acceptable salts and the pharmaceutically acceptable acid addition salts are crystalline materials which are more soluble in water and various hydrophilic solvents and which in comparison to the free acid form generally demonstrate higher melting points and an increased solubility.

Scheme 1

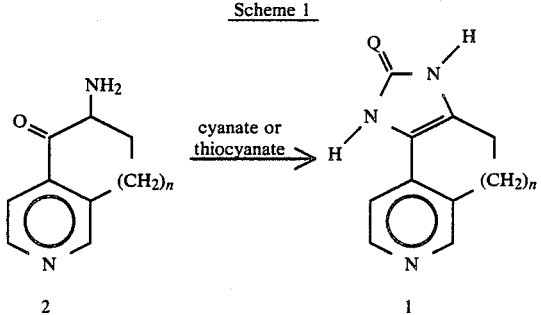

The compounds of this invention can be readily prepared by the acid catalyzed condensation of a cyclic alpha amino ketone of structure 2 with a cyanate or thiocyanate salt as shown in scheme 1. This condensation reaction is performed by allowing the structure 2 compound to react with a cyanate or thiocyanate salt, preferably sodium or potassium cyanate or thiocyanate. The reaction is acid catalyzed and the additional presence of a mild acid, for example, a dilute mineral acid such as dilute hydrochloric acid, sulfuric acid, or phosphoric acid, a carboxylic acid such as acetic acid, trifluoroacetic acid, benzoic acid, or formic acid, or a sulfonic acid such as methanesulfonic acid or p-toluenesulfonic acid in the reaction mixture is preferred. Preferably the solvent will act as the acid catalyst. This reaction is performed by mixing about 1 molar equivalent of the cyclic alpha amino ketone with about 1 to about 5 molar equivalents, preferably about 2 or 3 molar equivalents of the cyanate or thiocyanate salt in a suitable solvent. The reaction is allowed to proceed for about 5 minutes to about 10 hours depending on, for example, the solvent and the temperature which can be from about 0° C. to about 100° C. Conveniently the reaction can be carried out at room temperature, i.e. about 25° C., and this is preferred. Suitable solvents for this reaction can be any non-reactive solvent such as water or a water miscible solvent, for example, an organic acid such as acetic acid; an alcohol such as methanol or ethanol; or an ether such as tetrahydrofuran or p-dioxan. Preferably any non-aqueous solvent will be mixed with water. The preferred solvent is water.

The product of this reaction can be isolated and purified by any suitable art known procedures such as by evaporation of the reaction solvent. The product can be successfully purified by recrystallization from a mixture of ethanol and methanol. Conveniently when the solvent is a mixture of acetic acid and water the product separates from the reaction mixture as a crystalline substance which can then readily be isolated by filtration.

The cyclic alpha amino ketones of structure 2 are prepared from the corresponding cyclic ketone of structure 3 via the oxime of structure 3A and the para toluene sulfonyl, tosyl (Ts), derivative of structure 3B as illustrated in Scheme 2. The oxime of structure 3A is readily prepared from the cyclic ketone of structure 3 by any method known to be useful for this conversion, for example, by reacting the cyclic ketone with hydroxylamine. The oxime derivative is then converted to the tosyl derivative of structure 3B by any standard technique such as by reaction with tosyl chloride in the presence of a proton acceptor such as triethylamine. The structure 3B tosyl derivative is then converted to the amino ketone utilizing the Neber rearrangement, a well known means of converting ketoximes to alpha amino ketones and is discused in, for example, March, Advanced Organic Chemistry: Reactions, Mechanisms, and Structure, McGraw-Hill Book Company, New York, 1968, page 815–16, and is reviewed in C. O'Brien, Chem. Revs. 64, 81 (1964); D. J. Cram, Fundenmentals of Carbanion Chemistry (Academic Press, New York, 1965), p. 249; C. G. McCarty in S. Patai, Ed., Chemistry of the Carbon-Nitrogen Double Bond (Interscience, New York, 1970) p. 4471; T. S. Stevens, W. E. Watts, Selected Rearrangements 1973, p. 138; Y. Tamura et al., Synthesis 1973, 215; and R. F. Parcell, J. C. Sanchez, J. Org Chem. 46, 5229 (1981).

Scheme 2

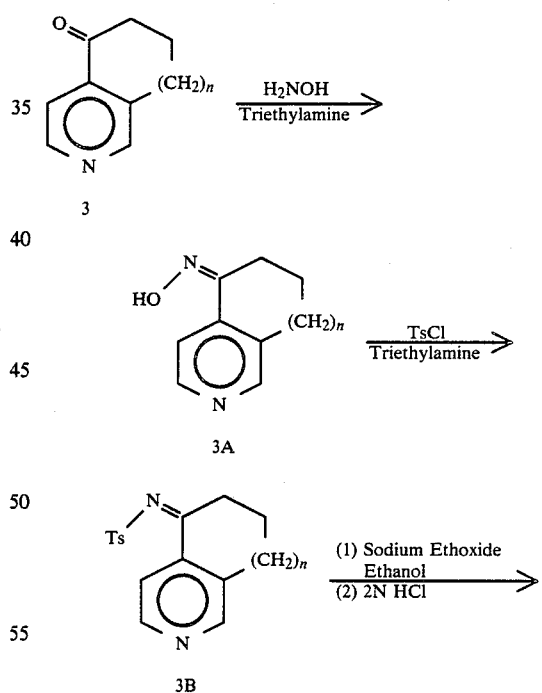

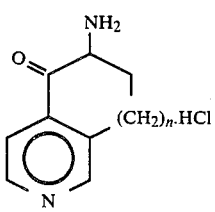

The compound of structure 3 wherein n is the integer 1 is known from J. Epsztain and A. Bieniek, *J. Chem. Soc. Perkin Trans.* 1, 213 (1985). This compound and the compounds wherein n is zero or the integer 2 can be prepared from the corresponding compound of structure 4 via the N-oxide derivative of structure 4A, the acetate (AcO) derivative of structure 4B, and the alcohol derivative of structure 4C as illustrated in Scheme 3.

The N-oxide derivatives are easily prepared by any means generally by those skilled in the art such as by treating a compound of structure 4 with hydrogen peroxide in acetic or formic acid. The acetate derivatives are then readily prepared by heating the N-oxide, preferably to the reflux temperature in a mixture of the corresponding N-oxide derivative of structure 4A and acetic anhydride. The acetate derivative is then converted into the alcohol by simple ester hydrolysis, for example, by heating a solution of the acetate in aqueous acid such as hydrochloric acid (5N). The cyclic ketones of structure 3 are then prepared from the corresponding alcohol of structure 4 by oxidation utilizing any effective means generally known to those skilled in the art taking into consideration that the oxidizing agent must not oxidize other funtionalities in the molecule such as the amine nitrogen. Applicants have oxidized the alcohols of structure 4 by use of the Swern reactions, that is, by treatment of the alcohol with a mixture of dimethylsulfoxide (DMSO) and oxalyl chloride followed by addition of a proton acceptor such as triethylamine.

Scheme 3

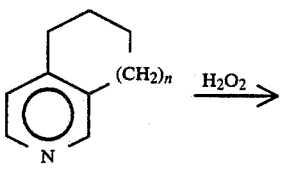

4

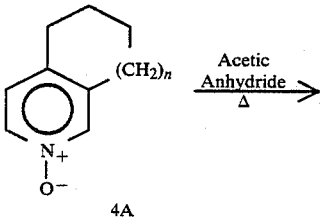

4A

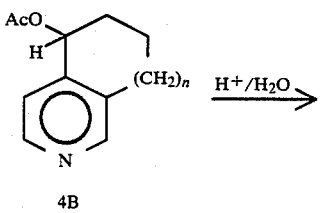

4B

-continued
Scheme 3

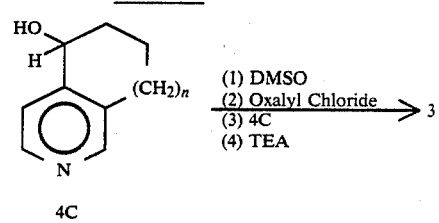

4C

The compound of structure 4 wherein n is the integer 1 is prepared by the catalytic reduction of isoquinoline using, for example, a palladium on carbon catalyst. The compounds of structure 4 wherein n is zero or the integer 2 are formed from the product of the 2+4, Diels-Alder like, addition reaction of 1,2,4-triazine with the in situ condensation product of cyclopentanone or cycloheptanone and pyrrolidine as illustrated in scheme 4 and described by D. L. Boger, et al., *J. Org. Chem.* 47, 895 (1982). The in situ condensation is facilitated by a dehydrating agent such as 4A molecular seives. The product of the 2+4 addition reaction upon spontaneous loss of pyrrolidine and molecular nitrogen yields the desired product of structure 4. The compound 1,2,4-triazine is known from W. W. Pandler and T. K. Chen, *J. Heterocyclic Chem.* 767 (1970).

Scheme 4

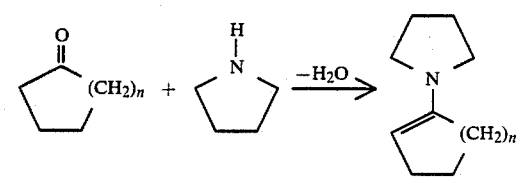

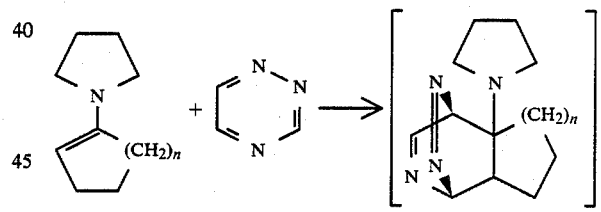

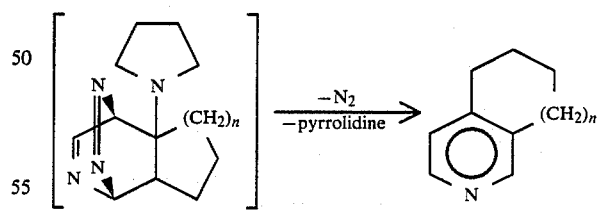

4

The compounds of structure 1 are cardiotonic agents useful in the treatment of heart failure and are believed to function by stengthening the heart muscle by virtue of their ability to enhance myocardial contractile force and reducing work load by virtue of their vasodilator activity. The utility of the structure 1 compounds as cardiotonic agents may be determined by administering the test compound (0.1–100 mg/kg) intraveneously, intraperitoneally, intraduodenally, or intragastrically in a suitable vehicle to a mongrel dog (either sex). The test dogs are anesthetized and prepared by isolating a suitable artery (e.g., femoral or common carotid) and vein (e.g., femoral or external jugular) and introducing polyethylene catheters filled with 0.1% Heparin-Sodium to record arterial blood pressure and administer compounds, respectively. The chest is opened by splitting the sterum at the midline or by an incision at the left fifth intercostal space, and a pericardial cradle is formed to support the heart. A Walton-Brodie strain gage is sutured to the right or left ventricle to monitor myocardial contractile force. An electromagnetic flow probe may be placed around the root of the ascending aorta for measuring cardiac output less coronary blood flow. A catheter may also be put into the left atrium or the left ventricle of the heart to record left atrial pressure or left ventricular pressure. Heart failure is induced by administering sodium pentobarbital (20 to 40 mg/kg) followed by a continuous infusion of 0.25–2 mg/kg/min. or propranolol hydrochloride (4 mg/kg) followed by a continuous infusion of 0.18 mg/kg/min. to the blood perfusing the heart. Following administration of either of the cardiac depressants, the right atrial pressure dramatically increases and cardiac output is severely depressed. Reversal of these effects by the test compound indicates cardiotonic activity.

The amount of the active ingredients to be administered can vary widely according to the particular dosage unit employed, the period of treatment, the age and sex of the patient treated, and the nature and extent of the disorder treated. The total amount of the active ingredient to be administered will generally range from about 0.1 mg/kg to 100 mg/kg and preferably from 0.3 mg/kg to 10 mg/kg. A unit dosage may contain from 5 to 500 mg of active ingredient, and can be taken one or more times per day. The active compound of formula 1 can be administered with a pharmaceutical carrier using conventional dosage unit forms either orally, parenterally, or topically.

As used herein, the term "patient" is taken to mean warm blooded animals, for example, birds such as chickens and turkeys, and mammals such as sheep, horses, cattle, pigs, dogs, cats, rats, mice, and primates including humans.

The preferred route of administration is oral administration. For oral administration the compounds can be formulated into solid or liquid preparations such as capsules, pills, tablets, troches, lozenges, melts, powders, solutions, suspensions, or emulsions. The solid unit dosage forms can be a capsule which can be of the ordinary hard- or soft-shelled gelatin type containing, for example, surfactants, lubricants, and inert fillers such as lactose, sucrose, calcium phosphate, and cornstarch. In another embodiment the compounds of this invention can be tableted with conventional tablet bases such as lactose, sucrose, and cornstarch in combination with binders such as acacia, cornstarch, or gelatin, disintegrating agents intended to assist the break-up and dissolution of the tablet following administration such as potato starch, alginic acid, corn starch, and guar gum, lubricants intended to improve the flow of tablet granulations and to prevent the adhesion of tablet material to the surfaces of the tablet dies and punches, for example, talc, stearic acid, or magnesium, calcium, or zinc stearate, dyes, coloring agents, and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and the polyethylene alcohols, either with or without the addition of a pharmaceutically acceptably surfactant, suspending agent, or emulsifying agent.

The compounds of this invention may also be administered parenterally, that is, subcutaneously, intravenously, intramuscularly, or interperitoneally, as injectable dosages of the compund in a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethyleneglycol) 400, an oil, a fatty acid, a fatty acid ester or glyceride, or an acetylated fatty acid glyceride with or without the addition of a pharmaceutically acceptable surfactant such as a soap or a detergent, suspending agent such as pectin, carbomers, methylcellulose, hydroxypropylmethylcellulose, or carboxymethylcellulose, or emulsifying agent and other pharmaceutically adjuvants. Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamines acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures. The parenteral compositions of this invention will typically contain from about 0.5 to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to about 15% by weight. The surfactant can be a single component having the above HLB or can be a mixture of two or more components having the desired HLB. Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The active ingredient may also be administered by means of a sustained release system whereby the compound of formula 1 is gradually released at a controlled, uniform rate form an inert or bioerodible carrier by means of diffusion, osmosis, or disintegration of the carrier during the treatment period. Controlled release drug delivery systems may be in the form of a patch or bandage applied to the skin or to the buccal, sublingual, or intranasal membranes, or a gradually eroding tablet or capsule or a gastrointestinal reservoir administered orally. Administration by means of such sustained release delivery systems permits the tissues of the body to be exposed constantly for a prolonged time period to a therapeutically or prophylactically effective dosage of a compound of formula 1. The unit dosage of the compound administered by means of a sustained release system will approximate the amount of an effective daily dosage multiplied by the maximum number of days during which the carrier is to remain on or in the body of the host. The sustained release carrier may be in the form of a solid or porous matrix or reservoir and may be formed from one or more natural or synthetic polymers, including modified or unmodified cellulose, starch, gelatin, collagen, rubber, polyolefins, polyamides, polyacrylates, polyalcohols, polyethers, polyesters, polyurethanes, polysulphones, polysiloxanes, and polyimides as wells as mixtures and copolymers of these polymers. The compounds of formula 1 may be incorporated in the sustained release carrier in a pure form or may be dissolved in any suitable liquid or solid vehicle, including the polymer of which the sustained release carrier is formed.

EXAMPLES

The following specific examples illustrate the preparation of the compounds of this invention as well as the pharmaceutical compositions containing these compounds but are not intended to limit the scope of the invention.

EXAMPLE 1

Preparation of 1,3,4,5-tetrahydro-2H-Imidazo[4,5-f]isoquinolin-2-one

A. Preparation of 5-hydroxyiminosoquinoline (Structure 3A: n=1)

Isoquinolin-5-one (21.57 g, 0.147M) and hydroxylamine (15.55 g, 0.22M) together with approximately 300 ml of dry ethanol and 75 ml of pyridine was stirred at reflux temperature of the mixture for 6 hours. The solvent was then removed by evaporation and the residue was dissolved in a mixture of diethyl ether and water (600 ml, ca. 1:1). The organic phase was separated and extracted with water to remove residual pyridine, washed with saturated, aqueous solution of sodium chloride and dried over magnesium sulfate crystals. The inorganic matter was removed by filtration and the solvent by evaporation leaving 14.7 grams of the desired product (61.7% yield).

B. Preparation of the tosyl ester of 5-hydroxyiminoisoquinoline (Structure 3B: n=1)

Tosyl chloride (20.7 g, 0.109M) was added portionwise over five minutes to a solution of 5-hydroxyiminoisoquinoline (14.7 g, 0.0906M) in dry pyridine (ca 200 ml) at 0° C. The mixture was then stirred at ~0° C. for 2 hours after addition was complete, cooled at about 4° C. for 48 hours, and finally quenched with about 1200 ml of water. The solid product was collected by filtration and dried (75.9%), m.p. 125°-127° C. (dec.).

C. Preparation of 6-aminoisoquinolin-5-one (Structure 2: n=1)

Spherical sodium (2.37 g, 0.103M) was aded to dry ethanol (50 ml) and stirred until the sodium had completely dissolved. A mixture of the tosyl ester of 5-hydroxyiminoisoquinoline (0.0687M) and ethanol (350 ml) was added over a 5 minute period then allowed to react at room temperature for ~2½ hours and subsequently at ~4° C. overnight. The mixture was added to diethyl ether (ca. 2½ l) then filtered to remove the precipitate. The filtrate was extracted with hydrochloric acid (~400 ml, 2N HCl) and the solvent removed by evaporation to yield the desired product (70.0%).

D. Preparation of 1,3,4,5-tetrahydro-2H-imidazo[4,5-f]isoquinoline-2-one (Structure 1: Q=0, n=1)

Potassium cyanate (8.63 g, 0.106 mole) was added to a solution of 6-aminoisoquinolin-5-one (5.0 g, 0.0213 mole) in hydrochloric acid (pH=1) while maintaining the acidity constant by subsequent addition of concentrated hydrochloric acid. After stirring for about 1½ hours, the product precipitated andwas obtained by filtration. Recrystallization from 50% aqueous ethanol gave 1.03 g (25%) of the desired product, m.p. >310° C.

Calculated for $C_{10}H_9N_3O \cdot HCl$: C, 53.70; H, 4.51; N, 18.78. Found (second run): C, 53.47 (53.54); H, 4.52 (4.75); N, 18.56 (18.38).

EXAMPLE 2

Tablets are prepared each having the composition:

| | |
|---|---|
| 1,3,4,5-Tetrahydro-2H—imidazo[4,5-f]isoquinolin-2-one | 250 mg |
| starch | 40 mg |
| talc | 10 mg |
| magnesium stearate | 10 mg |

EXAMPLE 3

Capsules are prepared each having the composition:

| | |
|---|---|
| 1,3,4,5-Tetrahydro-2H—imidazo[4,5-f]isoquinolin-2-one | 400 mg |
| talc | 40 mg |
| sodium carboxymethylcellulose | 40 mg |
| starch | 120 mg |

We claim:
1. A compound of the structure:

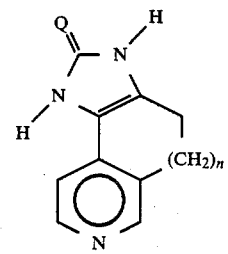

wherein
Q is a divalent sulfur or oxygen atom; and
n is 0 or the integer 1 or 2
or a pharmaceutically acceptably salt thereof.
2. A compound of claim 1 wherein Q is a divalent oxygen atom.
3. A compound of claim 1 wherein n is the integer 1.
4. A compound of claim 1 wherein n is the integer 1.
5. A method of treating heart failure in a patient in need thereof which comprises administering to the patient a cardiotonically effective amount of a compound of the structure:

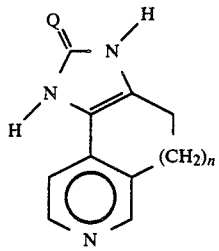

wherein

Q is a divalent sulfur or oxygen atom; and n is 0 or the integer 1 or 2 or a pharmaceutically acceptably salt thereof.

6. A method of claim 5 wherein Q is a divalent oxygen atom.

7. A method of claim 5 wherein n is the integer 1.

8. A method of claim 6 wherein n is the integer 1.

9. A method of enhancing myocardial contractile force in a patient in need thereof which comprises administering to the patient an effective amount of a compound of the structure:

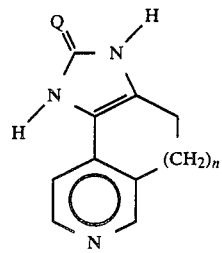

wherein
  Q is a divalent sulfur or oxygen atom; and
  n is 0 or the integer 1 or 2
or a pharmaceutically acceptably salt thereof.

10. A method of claim 9 wherein Q is a divalent oxygen atom.

11. A method of claim 9 wherein n is the integer 1.

12. A method of claim 10 wherein n is the integer 1.

13. A pharmaceutical composition useful for treating heart failure in a patient in need thereof, comprising a compound of the structure:

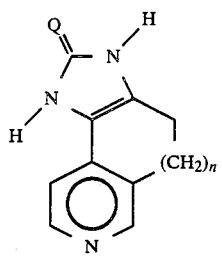

wherein
  Q is a divalent sulfur or oxygen atom; and
  n is 0 or the integer 1 or 2
or a pharmaceutically acceptable salt thereof and a pharmaceutically acceptable carrier and wherein the active ingredient is administered to the patient in a cardiotonically effective amount.

* * * * *